United States Patent [19]
Deghenghi

[11] Patent Number: 5,807,985
[45] Date of Patent: *Sep. 15, 1998

[54] OLIGOPEPTIDE COMPOUNDS CONTAINING D-2-ALKYLTRYPTOPHAN CAPABLE OF PROMOTING THE RELEASE OF GROWTH HORMONE

[76] Inventor: Romano Deghenghi, Chesaux-Dessus, St. Cergue, Switzerland, CH-1264

[ * ] Notice: The term of this patent shall not extend beyond the expiration date of Pat. No. 5,795,957.

[21] Appl. No.: 871,415

[22] Filed: Jun. 9, 1997

Related U.S. Application Data

[60] Provisional application No. 60/019,565, Jun. 11, 1996.
[51] Int. Cl.$^6$ ............................. C07K 5/00; A61K 38/00
[52] U.S. Cl. ............................. 530/331; 530/330; 514/2; 514/18; 514/19; 514/414; 548/455
[58] Field of Search .................... 514/2, 18, 19; 530/330, 331; 548/455

[56] References Cited

U.S. PATENT DOCUMENTS

| | | | |
|---|---|---|---|
| 4,228,155 | 10/1980 | Momany | 424/177 |
| 4,411,890 | 10/1983 | Momany | 424/177 |
| 4,839,344 | 6/1989 | Bowers | 514/16 |

*Primary Examiner*—Cecilia J. Tsang
*Assistant Examiner*—Cecilia Wang
*Attorney, Agent, or Firm*—Pennie & Edmonds LLP

[57] ABSTRACT

A peptide of formula:

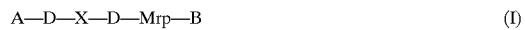

(I)

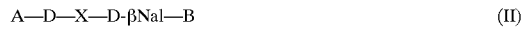

(II)

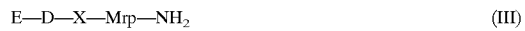

(III)

wherein A is hydrogen, 2-aminoisobutyryl, or 4-aminobutyryl;
D relates to the dextro isomer;
X is Mrp, wherein Mrp is a 2-alkyltryptophan of formula (IV):

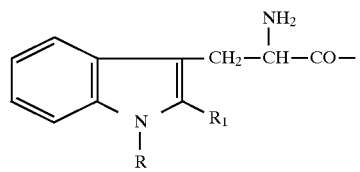

wherein R is hydrogen, CHO, $SO_2CH_3$, mesylene-2-sulfonyl, $PO_3(CH_3)_2$, $PO_3H_2$, wherein $R_1$ is a $C_1$–$C_3$ alkyl group, or wherein X is a residue of protected serine, Ser (Y), wherein Y is benzyl, p-chlorobenzyl, 4-methoxybenzyl, 2,4,6-trimethoxybenzyl, or tert-butyl;
B is $NR_2R_3$, wherein $R_2$ and $R_3$, may be the same or different, are hydrogen, a $C_1$–$C_3$ alkyl group, an $OR_4$ group, wherein $R_4$ is hydrogen, a $C_1$–$C_3$ alkyl group or the C—Lys—$NH_2$ group, wherein C is Phe, Mrp or D—Mrp;
E is hydrogen, GAB or D—Mrp, and addition salts with pharmaceutically acceptable organic or inorganic acids of the peptide.

22 Claims, 4 Drawing Sheets

OLIGOPEPTIDE COMPOUNDS CONTAINING D-2-ALKYLTRYPTOPHAN CAPABLE OF PROMOTING THE RELEASE OF GROWTH HORMONE

This application claims the benefit of U.S. Provisional Ser. No. 60/019,565, filed Jun. 11, 1996.

FIELD OF THE INVENTION

The present invention relates to oligopeptide compounds containing at least one D-2-alkyltryptophan amino acid and which are capable of releasing growth hormone (GH) from somatotrophs. More particularly, the present invention relates to short chain oligopeptides containing one or two D-2-alkyltryptophan amino acids, with the peptide being capable of causing the release of growth hormone (GH) in animals. Surprisingly, these compounds are active when administered via an oral route.

BACKGROUND OF THE INVENTION

If sufficiently high growth hormone (GH) levels are achieved after the administration of compounds capable of inducing GH release, the increase of growth hormone (GH) levels in mammals can accelerate growth, increase muscular mass increase and enhance production of milk. It is known that the increase of growth hormone levels in mammals can be achieved by administering growth hormone release agents, such as, for example, growth hormone release hormones (GHRH).

The increase of growth hormone levels in mammals can also be obtained by administering growth hormone release peptides. See, for example, the following U.S. Pat. Nos.: 4,223,019, 4,223,020, 4,223,021, 4,224,316, 4,226,857, 4,228,155, 4,228,156, 4,228,157, 4,228,158, 4,410,512, 4,410,513, 4,411,890 and 4,839,344. Many of the peptides described in these patents have complex structures, and are difficult to synthesize, purify and/or formulate into convenient dosage forms. Additionally, some of these have in vitro activity, but do not exhibit in vivo activity. Further, some of these peptides are not active when administered orally.

Therefore, rather simple, short chain oligopeptides capable of promoting growth hormone release that can be easily and conveniently prepared and that can be easily purified and formulated into a dosage form that can be administered via the oral route are presently desired. In particular, those oligopeptides exhibiting in vivo activity when administered orally are sought.

SUMMARY OF THE INVENTION

The present invention thus relates to a short chain oligopeptide of the following formulae:

A—D—X—D—Arp—B           (I)

A—D—X—D-βNal—B           (II)

E—D—X—Arp—NH₂            (III)

wherein A is hydrogen, 2-aminoisobutyryl (i.e., alpha-aminoisobutyric acid or methyl alanine), or 4-aminobutyryl (i.e. gamma-aminoisobutyric acid);
D relates to the dextro isomer;
X is Arp, wherein Arp stands for a 2-alkyltryptophan of formula (IV):

wherein R is hydrogen, CHO, $SO_2CH_3$, mesitylene-2-sulfonyl, $PO_3(CH_3)_2$, $PO_3H_2$, wherein $R_1$ is a $C_1$–$C_3$ alkyl group (e.g., methyl, ethyl, propyl or isopropyl) or wherein X is a residue of protected serine, Ser-(Y), wherein Y can be benzyl, p-chlorobenzyl, 4-methoxybenzyl, 2,4,6-trimethoxybenzyl, tert-butyl, wherein B is $NR_2R_3$, wherein $R_2$ and $R_3$, which can be the same or different, are hydrogen, a $C_1$–$C_3$ alkyl group, an $OR_4$ group, wherein $R_4$ is hydrogen, a $C_1$–$C_3$ alkyl, or a C—Lys—$NH_2$ group, wherein C is Phe, Arp or D—Arp; and wherein E is hydrogen, GAB or D—Arp. Of course, D-βNal (Nal being naphthyl alanine) is well known to those skilled in the art and needs no further definition.

DETAILED DESCRIPTION OF THE PREFERRED EMBODIMENTS

The present invention lies on the discovery that all of the different short-chain oligopeptides which promote the release and increase of growth hormone levels in blood of animals include in the peptide chain a D-isomer of 2-alkyltryptophan. In a completely surprising manner it has now been found that very short oligopeptides, having at least one D—Arp residue, have activity releasing growth hormone (GH) from somatotrophs. Another unexpected distinctive feature of the present invention is the very high potency and the favorable oral activity/oral potency ratio that even the smallest tripeptides of the series exhibit.

The oligopeptides within the scope of the present invention are defined by a short chain oligopeptide of formula (I), (II), or (III):

A—D—X—D—Arp—B           (I)

A—D—X—D-βNal—B           (II)

E—D—X—Arp—NH₂            (III)

wherein
A is hydrogen, 2-aminoisobutyryl (i.e., alpha-aminoisobutyric acid), or 4-aminobutyryl (i.e. gamma-aminoisobutyric acid), D relates to the dextro isomer,
X is Arp, wherein Arp stands for 2-alkyltryptophan of formula (IV):

wherein R is hydrogen, CHO, SO$_2$CH$_3$, mesitylene-2-sulfonyl, PO$_3$(CH$_3$)$_2$, PO$_3$H$_2$, wherein R$_1$ is a C$_1$–C$_3$ alkyl group (e.g., methyl, ethyl, propyl or isopropyl) or wherein X is a residue of protected serine, Ser (Y), wherein Y can be benzyl, p-chlorobenzyl, 4-methoxybenzyl, 2,4,6-trimethoxybenzyl, tert-butyl, wherein B is NR$_2$R$_3$, wherein R$_2$ and R$_3$, which can be the same or different, are hydrogen, a C$_1$–C$_3$ alkyl group, an OR$_4$ group, wherein R$_4$ is hydrogen, a C$_1$–C$_3$ alkyl, or a C—Lys—NH$_2$ group, wherein C is Phe, Arp or D—Arp, and wherein E is hydrogen, GAB or D—Arp, along with the addition salts with pharmaceutically acceptable organic or inorganic acids of any one of these short chain oligopeptides.

The abbreviations for the residues of amino acids herein used are in agreement with the standard nomenclature for the peptides:
Lys=L-Lysine
Moreover,
Aib=2-aminoisobutyryl;
GAB=4-aminobutyryl;
Arp=2-alkyltryptophan;
Bzl=benzyl;
p-Cl—Bzl=p-chlorobenzyl;
Mob=4-methoxybenzyl;
Mrp=2-methyltryptophan;
Tmob=2,4,6-trimethoxybenzyl;
tbu=tert-butyl;
For=formyl;
Mts=mesitylene-2-sulfonyl.

According to the present invention, alkyl means lower alkyl, comprising from 1 to 3 carbon atoms. Examples of lower alkyl are methyl, ethyl, propyl, isopropyl. Among these, the methyl group is most preferred.

All the three letter-abbreviations of the amino acids preceded by a "D" indicate the D-configuration of the amino acid residue. When the amino acid is referred to with the only three-letter abbreviation, it has L configuration.

The preferred growth hormone-release compounds of the present invention are GAB—D—Mrp—D—Mrp—Phe—Lys—NH$_2$; GAB—D—Mrp—D—Mrp—Mrp—Lys—NH$_2$; Aib—D—Mrp—D—Mrp—NH$_2$; Aib—D—Mrp—Mrp—NH$_2$; Aib—D—Ser(Bzl)—D—Mrp—NH$_2$; GAB—D—Mrp—D—βNal—Phe—Lys—NH$_2$; GAB—D—Mrp—D—Mrp—D—Mrp—Lys—NH$_2$; D—Mrp—D—Mrp—Mrp—NH$_2$; GAB—D—Mrp—Mrp—NH$_2$; and D—Mrp—Mrp—NH$_2$; wherein Mrp, GAB, and Aib are as defined above. The addition salts with pharmaceutically acceptable organic or inorganic acids of any one of these oligopeptides can also be used.

These compounds are preferably administered by the oral route, but they also can be administered intranasally, buccally or parenterally. These compounds (i.e., oligopeptides of the present invention) can be formulated into controlled release dosage forms, such as, biodegradable microcapsules, microspheres, subcutaneous implants and the like. Other controlled release dosage forms, though not specifically listed, are known to those skilled in the art and are within the scope of the present invention.

The oligopeptide compounds according to the present invention can be synthesized according to the usual methods of peptide chemistry, both solid-phase and solution, or by means of the classical methods known in the art. The solid-phase synthesis starts from the C-terminal end of peptide. A suitable starting material can be prepared, for example, by attaching the required protected alpha-amino acid to a chloromethylated resin, a hydroxymethylated resin, a benzylhydrylamine resin (BHA), or to a para-methylbenzylhydrylamine resin (p-Me—BHA). More particularly, for example, a chloromethylated resin is sold with the Trade Mark BIOBEADS® SX 1 by BioRad Laboratories, Richmond, Calif. The preparation of the hydroxymethyl resin is described by Bodansky et al., Chem. Ind. (London) 38, 15997, (1966). The BHA resin is described by Pietta and Marshall, Chem. Comm., 650 (1970) and is commercially available from Peninsula Laboratories Inc., Belmont, Calif.

After the starting attachment, the alpha-amino acid-protecting group can be removed by means of different acid reagents, comprising trifluoroacetic acid (TFA) or hydrochloric acid (HCl) dissolved in organic solvents at room temperature. After the removal of the alpha-amino acid-protecting group, the remaining protected amino acids can be coupled step by step in the desired order. Each protected amino acid can generally be reacted in excess of about three times using a suitable carboxyl activating group, such as dicyclohexylcarbodiimide (DCC) or diisopropylcarbodiimide (DIC) dissolved, for example, in methylene chloride (CH$_2$Cl$_2$) or dimethylformamide (DMF) and mixtures thereof. After the desired amino acid sequence has been completed, the desired peptide can be cleaved from the supporting resin by treatment with a reagent such as hydrogen fluoride (HF), which not only cleaves the peptide from the resin, but also the more common protecting groups of the lateral chains. When a chloromethylated resin or a hydroxymethylated resin is used, the treatment with HF leads to the formation of the acid peptide in free form. When a BHA or p-Me-BHA resin is used, the treatment with HF directly leads to the formation of the amide peptide in free form.

The above discussed solid-phase procedure is known in the art and was described by Atherton and Sheppard, Solid Phase Peptide Synthesis (IRL Press, Oxford, 1989).

Some methods in solution, which can be used to synthesize the peptide moieties of the present invention are detailed in Bodansky et al., Peptide Synthesis, 2nd edition, John Wiley & Sons, New York, N.Y. 1976 and from Jones, The Chemical Synthesis of Peptides, (Clarendon Press, Oxford, 1994).

These compounds can be administered to animals and humans at effective doses which can be easily determined by one of ordinary skill in the art and which can vary according to the specie, age, sex and weight of the subject to be treated. For example, in humans, when intravenously administered, the preferred dose falls in the range from about 0.1 µg to about 10 µg of total peptide per kg of body weight. When orally administered, typically higher amounts are necessary. For example, in humans for the oral administration, the dosage level is typically from about 30 µg to about 1000 µg of peptide per kg of body weight. The exact level can be easily determined empirically by the skilled artisan.

Compositions which comprise as active ingredient the organic and inorganic addition salts of the above described oligopeptides and their combinations, optionally, in admixture with a vehicle, diluent, matrix or delayed release coating, are also within the scope of the present invention. The delayed release pharmaceutical forms, comprising biodegradable polymer matrixes, suitable for subcutaneous implant are particularly interesting. Examples of these matrices are described in WO9222600 and WO9512629. All patents and references cited herein are incorporated herein by reference in their entirety and for all purposes.

EXAMPLES

The following examples are provided as illustrations of preferred embodiments of the present invention and are not intended to limit the breadth and scope of the invention as is readily understood by those skilled in the art. These examples illustrate the method of making and biological activity of the preferred peptides of the invention.

Example 1

Making use of the solid-phase peptide synthesis technique as described in "Solid phase peptide synthesis" by E. Atherton and R. C. Sheppard, IRL Press, Oxford University Press, 1984, using fluorenylmethoxycarbonyl (Fmoc) as the protecting group, the peptide:

GAB—D—Mrp—D—Mrp—Phe—Lys—NH₂ was prepared, wherein Mrp is 2-methyltryptophan, M.W. 779.9, found 778.4; purity (HPLC) 98.0%

Example 2

Analogous to Example 1, the following peptide was prepared:

GAB—D—Mrp—D—Mrp—Mrp—Lys—NH₂ wherein Mrp is 2-methyltryptophan, M.W. 830.8, found 831.3; purity (HPLC) 98.0%.

Example 3

Analogous to Example 1, the following peptide was prepared:

Aib—D—Mrp—D—Mrp—NH₂, wherein Mrp is 2-methyltryptophan, M.W. 502.6, found 503.3; purity (HPLC) 99.0%.

Example 4

Analogous to Example 1, the following peptide was prepared:

Aib—D—Mrp—Mrp—NH2, wherein Mrp is 2-methyltryptophan, M.W. 502.6, found 503.3; purity (HPLC) 99.0%.

Example 5

Analogous to Example 1, the following peptide was prepared:

Aib—D—Ser(Bzl)—D—Mrp—NH₂, wherein Mrp is 2-methyltryptophan, M.W. 479.6, found 480.5;
purity (HPLC) 99.0%.

Example 6

Analogous to Example 1, the following peptide was prepared:

GAB—D—Mrp—D-βNal—Phe—Lys—NH₂ wherein Mrp is 2-methyltryptophan, M.W. 774.8, found 775: purity (HPLC) 99.0%.

Example 7

Analogous to Example 1, the following peptide was prepared:

GAB—D—Mrp—D—Mrp—D—Mrp—Lys—NH₂ wherein Mrp is 2-methyltryptophan, M.W. 830.8, found 831.5: purity (HPLC) 99.0%.

Example 8

Analogous to Example 1, the following peptide was prepared:

D—Mrp—D—Mrp—Mrp—NH₂, wherein Mrp is 2-methyltryptophan, M.W. 617.7, found 618.3: purity (HPLC) 99.0%.

Example 9

Analogous to Example 1, the following peptide was prepared:

D—Mrp—Mrp—NH₂, wherein Mrp is 2-methyltryptophan, M.W. 417.5, found 418.3: purity (HPLC) 99.0%.

Example 10

Analogous to Example 1, the following peptide was prepared:

GAB—D—Mrp—Mrp—NH₂, wherein Mrp is 2-methyltryptophan, M.W. 502.6, found 503.2: purity (HPLC) 99.0%.

Example 11 Biological activity

In vivo activity of these compounds was determined in ten-day-old rats, which were subcutaneously (s.c.) injected with a dose of 300 µg/kg or with different doses in dose-response studies, according to methods described in detail by R. Deghenghi et al, *Life Sciences,* 54, 1321, (1994). The results are provided in Table 1 below. The released GH was measured 15 minutes after injection.

TABLE 1

| Peptide of example | Dose µg/kg s.c. | released GH (ng/ml) |
|---|---|---|
| 1 | 300 | 155.4 ∓ 19.7 |
| 2 | 300 | 165.4 ∓ 18.5 |
| 3 | 300 | 174.2 ∓ 25.9 |
| 4 | 300 | 64.2 ∓ 12.6 |
| 5 | 1.2 mg/kg | 59.4 ∓ 12.3 |
| 6 | 300 | 145.7 ∓ 9.0 |
| 7 | 300 | 91.2 ∓ 9.0 |
| 8 | 300 | 26.3 ∓ 5.0 |
| 9 | 300 | 27.0 ∓ 4.8 |
| 10 | 300 | 36.0 ∓ 9.5 |
| Controls | — | 15.7 ∓ 6.7 |

The data show that the peptides of Examples 1, 2, 3 and 6 are the most active.

Example 12

Figure 1A:
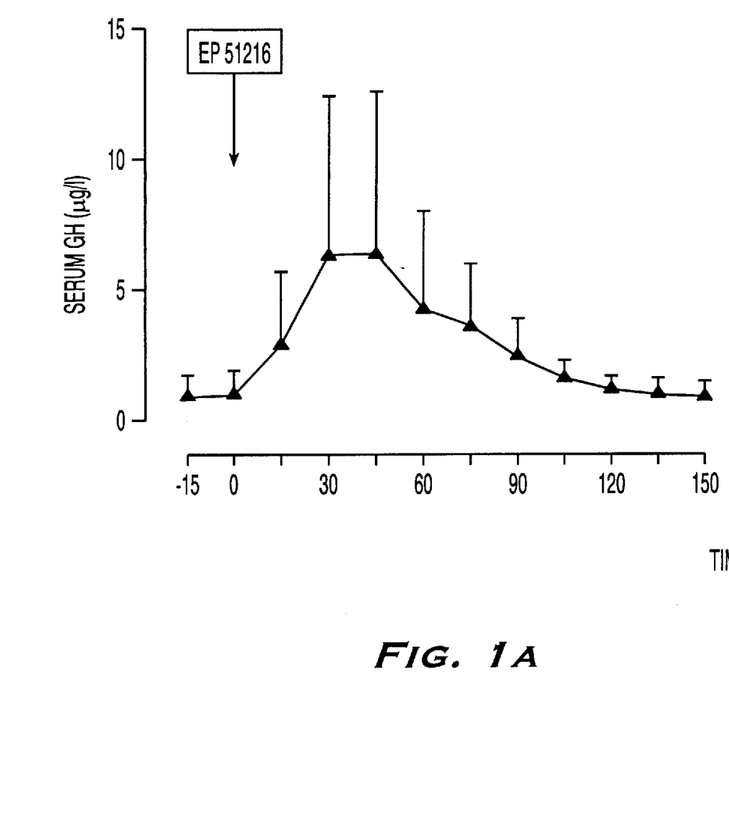
FIGS. 1A and 1B are graphs of the amount of growth hormone and cortisol released in humans after administration of GAB—D—Arp—D—Arp—Arp—Lys—$NH_2$.
Figure 1B:
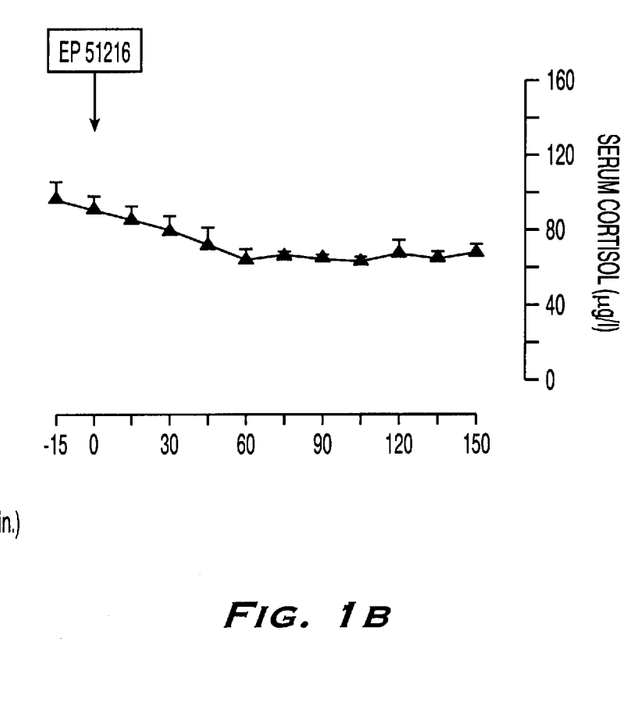

A capsule containing 20 mg of the peptide of Example 2 was orally administered to 5 healthy subjects (3 men and 2 women, ages 30 to 66) and serum growth hormone and cortisol levels were measured at various times after administration. Results are shown in FIGS. 1A and 1B. Surprisingly, growth hormone levels were increased without cortisol stimulation.

Examples 13–15

Figure 2:
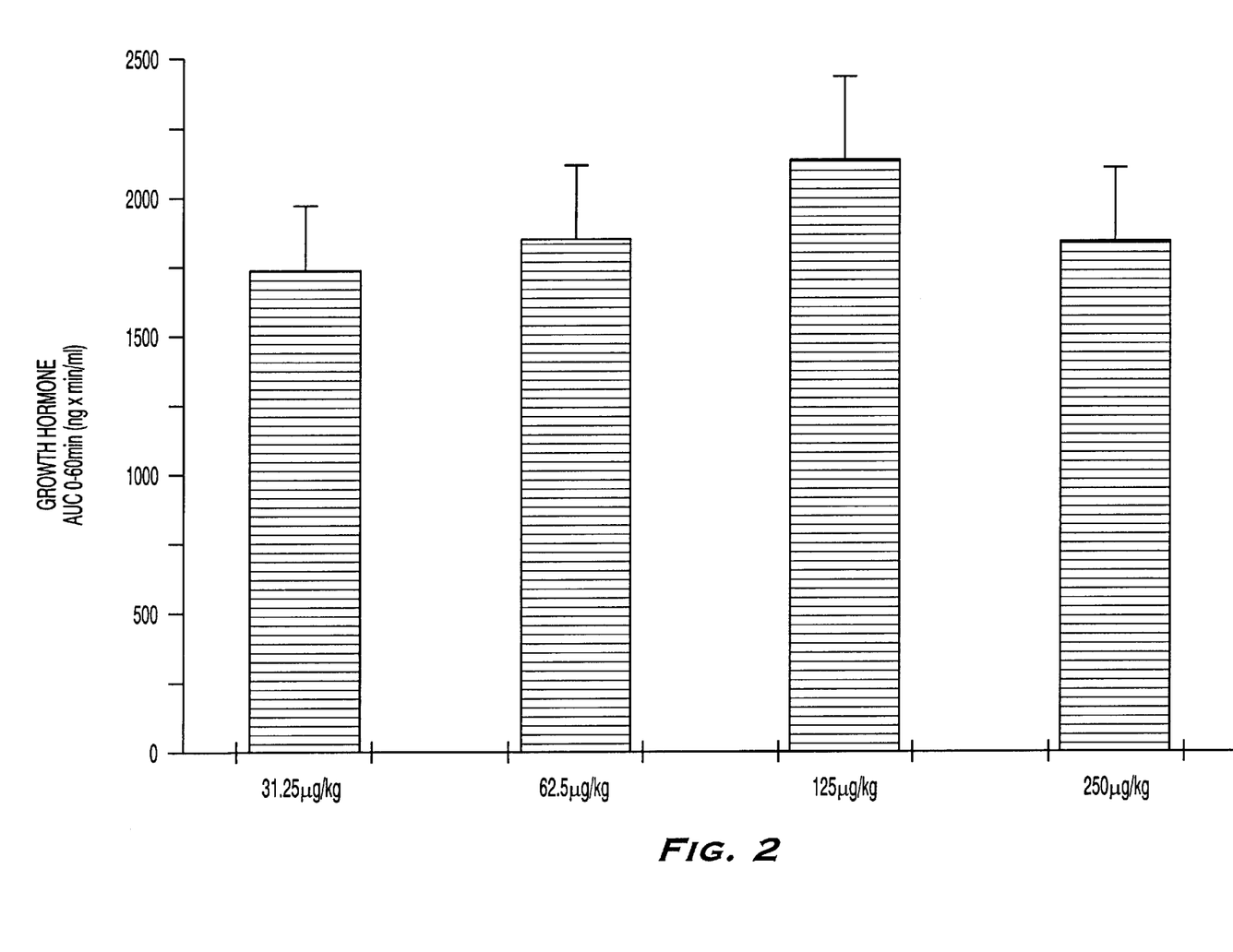
FIGS. 2–4 are graphs of the amount of growth hormone released in dogs after oral administration of various amounts of the peptide GAB—D—Arp—D-βNal—Phe—Lys—$NH_2$ (FIG. 2) and Aib—D—Arp—D—Arp—$NH_2$ (FIGS. 3 and 4).
Figure 3:
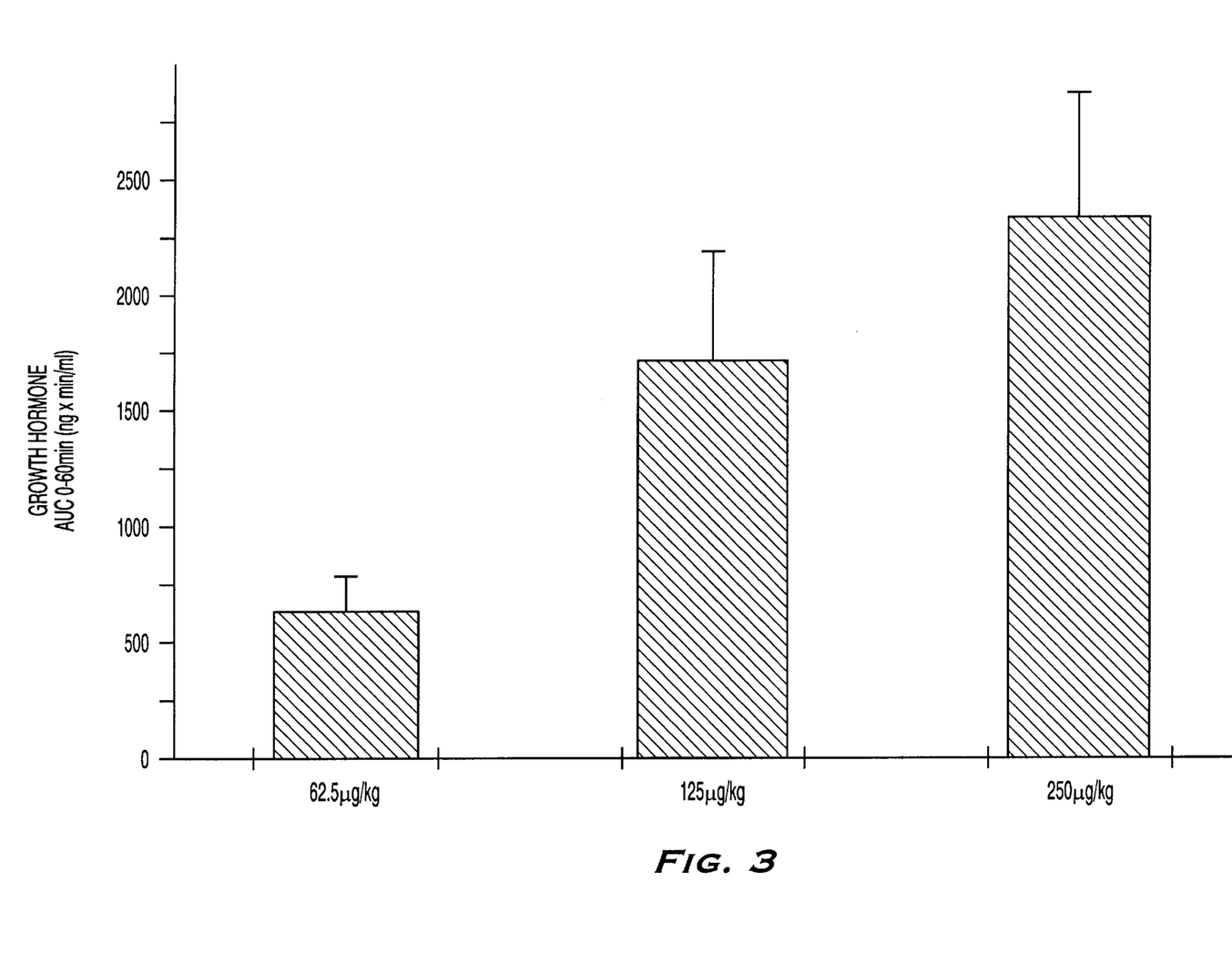
Figure 4:
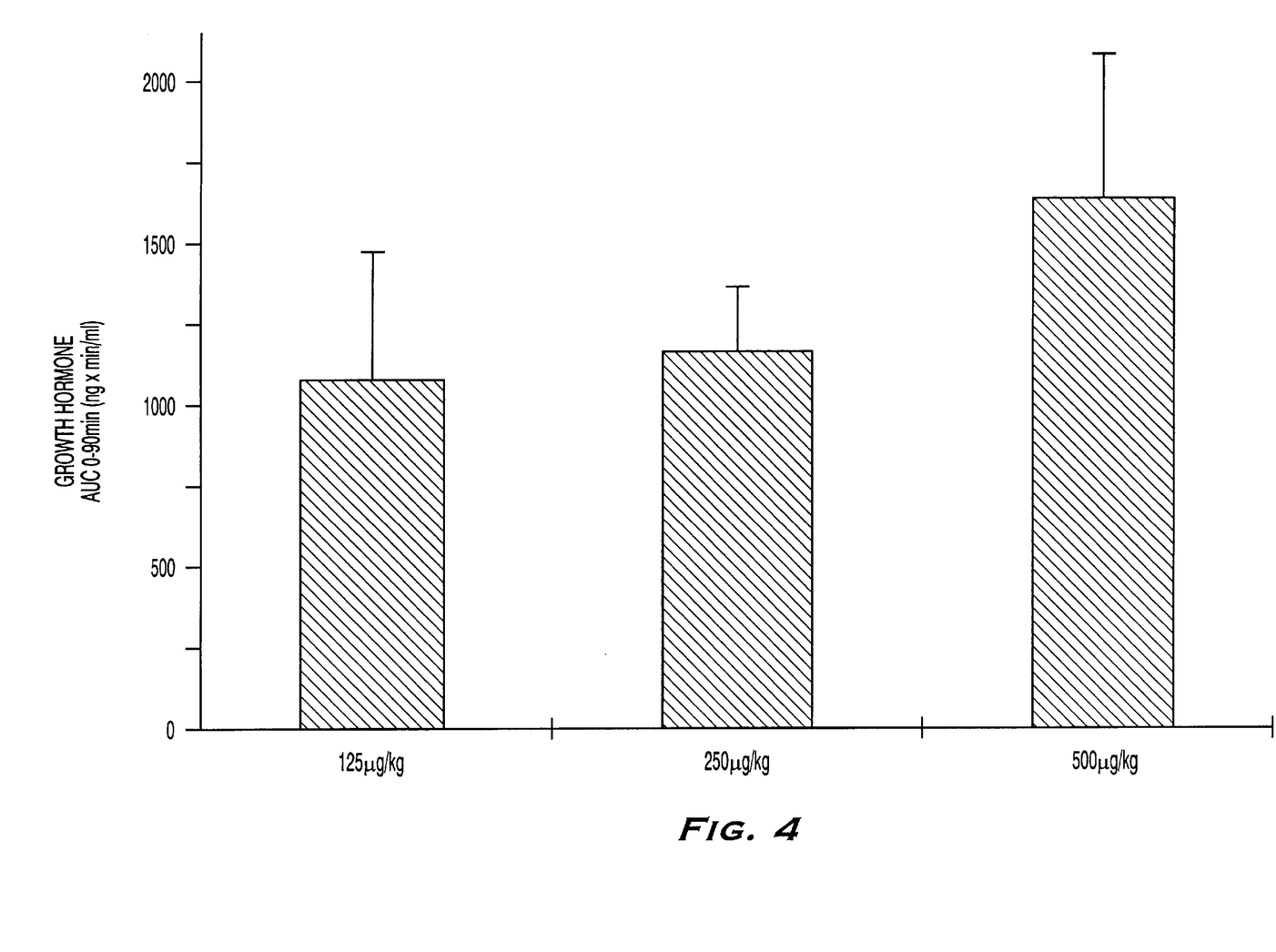

The peptides of Examples 2, 3 and 6 were selected for further study and were tested in vivo in adult dogs. The peptides were administered orally at a dosage of 1 mg/Kg body weight. Results are shown in FIGS. 2–4.

Example 16–17

The peptides of Examples 3 and 6 were further studied for inhibition of $^{125}$I—Tyr—Ala—HEXARELIN binding to human tissue. HEXARELIN is His—D—Mrp—Ala—Trp—D—Phe—Lys—NH$_2$ where Mrp is 2-methyltryptophan.

Tissue membranes (0.1 mg protein) obtained from the heart and hypothalamus of two different adult subjects were incubated in triplicate with a subsaturating concentration (34 pM, about 48,000 cpm, for heart tissue and 42 pM, about 60,000 cpm, for hypothalamus tissue) of $^{125}$I—Tyr—Ala—HEXARELIN for 40 min at 0° C. in the absence and in the presence of increasing concentrations of the indicated unlabelled peptides. The value in parentheses represents the percent of inhibition of $^{125}$1I—Tyr—Ala—HEXARELIN specifically bound. Results are shown in the Tables below.

TABLE 2

Human heart tissue

| peptide concentration (nM) | HEXARELIN subject 1 | HEXARELIN subject 2 | Example 3 subject 1 | Example 3 subject 2 | Example 6 subject 1 | Example 6 subject 2 |
|---|---|---|---|---|---|---|
| 0 | 21.0 (0) | 23.9 (0) | 25.1 (0) | 24.6 (0) | 20.3 (0) | 24.0 (0) |
| 0.1 | 20.1 (4) | 22.8 (5) | 25.1 (0) | 24.5 (0) | 20.1 (1) | 23.8 (1) |
| 1 | 16.9 (20) | 17.3 (28) | 24.9 (1) | 24.5 (0) | 19.8 (3) | 23.5 (2) |
| 10 | 10.4 (51) | 10.5 (56) | 24.9 (1) | 24.0 (3) | 16.5 (19) | 19.2 (20) |
| 100 | 1.7 (92) | 2.4 (90) | 24.7 (2) | 24.1 (2) | 10.2 (50) | 11.2 (53) |
| 1000 | 0 (100) | 0 (100) | 24.4 (3) | 24.0 (3) | 4.0 (80) | 4.0 (83) |
| IC$_{50}$ value (nM) | 10.6 | 8.3 | inactive | inactive | 62.7 | 57 |
| mean IC$_{50}$ value (nM) | 9.5 | | — | | 59.8 | |
| comparative IC$_{50}$ value (HEXARELIN = 1) | 1 | | — | | 6 | |

TABLE 3

Human hypothalamus tissue

| peptide concentration (nM) | HEXARELIN subject 1 | HEXARELIN subject 2 | Example 3 subject 1 | Example 3 subject 2 | Example 6 subject 1 | Example 6 subject 2 |
|---|---|---|---|---|---|---|
| 0 | 11.2 (0) | 9.5 (0) | 11.0 (0) | 10.3 (0) | 10.2 (0) | 10.8 (0) |
| 0.1 | 10.7 (3) | 9.1 (4) | 9.8 (11) | 9.0 (13) | 9.1 (11) | 10.0 (7) |
| 1 | 9.6 (16) | 7.7 (19) | 8.3 (25) | 7.0 (32) | 8.8 (14) | 8.9 (18) |
| 10 | 5.2 (51) | 3.1 (67) | 3.9 (65) | 3.6 (75) | 3.8 (63) | 3.3 (69) |
| 100 | 1.2 (89) | 0.7 (93) | 1.0 (91) | 0.2 (98) | 2.1 (79) | 1.9 (82) |
| 1000 | 0 (100) | 0 (100) | 0 (100) | 0.1 (99) | 0.3 (97) | 0 (100) |
| IC$_{50}$ value (nM) | 8.9 | 5.0 | 6.0 | 3.6 | 6.2 | 4.5 |
| mean IC$_{50}$ value (nM) | 7.0 | | 4.8 | | 5.4 | |
| comparative IC$_{50}$ value (HEXARELIN = 1) | 1 | | 0.7 | | 0.8 | |

The specific binding of $^{125}$I—Tyr—Ala—HEXARELIN/0.1 mg membrane protein is expressed as a percent of total radioactivity added. The results show that the peptide of Example 3 exhibits potent binding to hypothalamus tissue with no binding to heart tissue, while the peptide of Example 3 also exhibits strong binding to hypothalamus tissue with only moderate binding to heart tissue.

While it is apparent that the invention herein disclosed is well calculated to fulfill the objectives stated above, it will be appreciated that numerous embodiments and modifications may be devised by those skilled in the art, and it is intended that the appended claims cover all such modifications and embodiments as fall within the true spirit and scope of the present invention.

What is claimed is:

1. A peptide of formula (I), (II), or (III):

A—D—X—D—Arp—B       (I)

A—D—Arp—D-βNal—B    (II)

E—D—Arp—Arp—NH$_2$  (III)

wherein A is hydrogen, Aib, or GAB, wherein Aib is 2-aminoisobutyryl and GAB is 4-aminobutyryl;
D relates to the dextro isomer;
Nal is naphthyl alanine;
X is a residue of protected serine, Ser(Y), or Arp, wherein Y is benzyl, p-chlorobenzyl, 4-methoxybenzyl, 2,4,6-trimethoxybenzyl, or tert-butyl, and Arp is a 2-alkyltryptophan of formula (IV):

wherein R is hydrogen, CHO, SO$_2$CH$_3$, mesitylene-2-sulfonyl, PO$_3$(CH$_3$)$_2$, or PO$_3$H$_2$, and R$_1$ is a C$_1$–C$_3$ alkyl group, B is NR$_2$R$_3$ or C—Lys—NH$_2$, wherein R$_2$ and R$_3$, which may be the same or different, are hydrogen, a C$_1$–C$_3$ alkyl group, an OR$_4$ group, wherein R$_4$ is hydrogen or a C$_1$–C$_3$ alkyl group, and C is Phe, Arp or D—Arp;
E is hydrogen, GAB or D—Arp; or a pharmaceutically acceptable addition salt of said peptide.

2. The peptide according to claim 1 wherein Arp is selected from the group consisting of 2-methyltryptophan, 2-ethyltryptophan, 2-propyltryptophan and 2-isopropyltryptophan and the pharmaceutically acceptable addition salt is derived from an organic or inorganic acid.

3. The peptide according to claim 1 wherein Arp is 2-methyltryptophan.

4. The peptide according to claim 1 wherein A is Aib or Gab.

5. The peptide according to claim 1 wherein B is C—Lys—NH$_2$.

6. The peptide according to claim 1 wherein formula (I) is

GAB—D—ArP—D—Arp—Phe—Lys—NH$_2$;

GAB—D—Arp—D—Arp—Arp—Lys—NH$_2$;

Aib—D—Arp—D—Arp—NH$_2$;

Aib—D—Ser(benzyl)—D—Arp—NH$_2$;

GAB—D—Arp—D—Arp—D—Arp—Lys—NH$_2$, or;

D—Arp—D—Arp—Arp—NH$_2$.

7. The peptide according to claim 6 wherein Arp is 2-methyltryptophan.

8. The peptide according to claim 1 wherein formula (I) is

Aib—D—Arp—D—Arp—NH$_2$ or

GAB—D—Arp—D—Arp—Phe—Lys—NH$_2$.

9. A method for promoting the release of growth hormone in an animal which comprises administering the peptide of claim 1 to a subject in need of such treatment.

10. The method according to claim 9 wherein the peptide is administered intravenously in an amount of about 0.1 μg to about 10 μg of total peptide per kg of body weight.

11. The method according to claim 9 wherein the peptide is administered orally in an amount of about 30 μg to about 1000 μg of peptide per kg of body weight.

12. A pharmaceutical composition comprising a therapeutically effective amount of at least one peptide of claim 1 as active ingredient in admixture with a pharmaceutically acceptable carrier or excipient.

13. The pharmaceutical composition according to claim 12 wherein said peptide is in the form of a pharmaceutically acceptable addition salt and the composition is in a form suitable for parenteral, intranasal, buccal or oral administration.

14. The pharmaceutical composition according to claim 12 wherein said carrier is a biodegradable polymer matrix so that the composition is in a controlled release dosage form.

15. The pharmaceutical composition according to claim 12 wherein said controlled release dosage form is a subcutaneous implant.

16. The peptide according to claim 1 wherein formula (II) is

GAB—D—Arp—D-βNal—Phe—Lys—NH$_2$.

17. The peptide according to claim 1 wherein formula (III) is

GAB—D—Arp—Arp—NH$_2$ or

D—Arp—Arp—NH$_2$.

18. A peptide having the formula Aib—D—Arp—Arp—NH$_2$, wherein Aib is 2-aminoisobutyryl and Arp is a 2-alkyltryptophan of formula (IV):

wherein R is hydrogen, CHO, SO$_2$CH$_3$, mesitylene-2-sulfonyl, PO$_3$(CH$_3$)$_2$, or PO$_3$H$_2$, and R$_1$ is a C$_1$–C$_3$ alkyl group, or a pharmaceutically acceptable addition salt of said peptide.

19. The peptide according to claim 1 wherein formula (I) is

GAB—D—Mrp—D—Mrp—Phe—Lys—NH$_2$;

GAB—D—Mrp—D—Mrp—Mrp—Lys—NH$_2$;

Aib—D—Mrp—D—Mrp—NH$_2$;

Aib—D—Ser(benzyl)—D—Mrp—NH$_2$;

GAB—D—Mrp—D—Mrp—D—Mrp—Lys—NH$_2$, or;

D—Mrp—D—Mrp—Mrp—NH$_2$;

wherein Mrp is 2-methyltryptophan.

20. The peptide according to claim 1 wherein formula (II) is GAB—D—Mrp—D-βNal—Phe—Lys—NH$_2$, wherein Mrp is 2-methyltryptophan.

21. The peptide according to claim 1 wherein formula (III) is GAB—D—Mrp—Mrp—NH$_2$ or D—Mrp—Mrp—NH$_2$, wherein Mrp is 2-methyltryptophan.

22. The peptide according to claim 18 wherein the formula is Aib—D—Mrp—Mrp—NH$_2$, wherein Mrp is 2-methyltryptophan.

* * * * *

UNITED STATES PATENT AND TRADEMARK OFFICE
CERTIFICATE OF CORRECTION

| | | |
|---|---|---|
| PATENT NO. | : | 5,807,985 |
| DATED | : | September 15, 1998 |
| INVENTOR | : | Romano Deghenghi |

It is certified that error appears in the above-identified patent and that said Letters Patent is hereby corrected as shown below:

Column 9, line 48 (claim 4, line 2): change "Gab" to --GAB--.

Column 9, line 54 (claim 6, line 3): change "ArP" to --Arp--.

Signed and Sealed this

Eighth Day of December, 1998

*Attest:*

BRUCE LEHMAN

*Attesting Officer*   *Commissioner of Patents and Trademarks*